United States Patent
Shelley et al.

(10) Patent No.: US 7,145,147 B1
(45) Date of Patent: Dec. 5, 2006

(54) APPARATUS AND METHODS OF DETERMINING CHEMICAL PROPERTIES OF A RESIN-BASED MATERIAL USING INFRARED ABSORBANCE

(75) Inventors: Paul H. Shelley, Lakewood, WA (US); Diane R. LaRiviere, Seattle, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/173,597

(22) Filed: Jun. 30, 2005

(51) Int. Cl.
*G01J 5/02* (2006.01)

(52) U.S. Cl. .......................... 250/339.11; 250/339.12; 250/341.8

(58) Field of Classification Search ........... 250/339.11, 250/341.8, 339.12
See application file for complete search history.

(56) References Cited

U.S. PATENT DOCUMENTS

| | | | |
|---|---|---|---|
| 5,091,647 A | 2/1992 | Carduner et al. | |
| 5,142,151 A | 8/1992 | Varnell et al. | |
| 5,208,648 A | 5/1993 | Batchelder et al. | |
| 5,258,825 A * | 11/1993 | Reed et al. | 356/402 |
| 5,381,228 A | 1/1995 | Brace | |
| 5,569,921 A * | 10/1996 | Sato et al. | 250/339.01 |
| 5,668,373 A * | 9/1997 | Robbat et al. | 250/339.12 |
| 6,330,387 B1 | 12/2001 | Salamon et al. | |
| 6,441,375 B1 | 8/2002 | Joseph et al. | |
| 6,784,431 B1 | 8/2004 | Shelley et al. | |
| 6,794,651 B1 | 9/2004 | Shelley et al. | |
| 6,797,957 B1 | 9/2004 | Shelley et al. | |
| 6,903,339 B1 | 6/2005 | Shelley et al. | |
| 6,906,327 B1 | 6/2005 | Shelley et al. | |
| 2003/0001119 A1 | 1/2003 | Takezawa et al. | |
| 2003/0230720 A1 | 12/2003 | Shelley et al. | |
| 2003/0232448 A1 | 12/2003 | Shelley et al. | |
| 2004/0099807 A1 | 5/2004 | Shelley et al. | |

* cited by examiner

*Primary Examiner*—David Porta
*Assistant Examiner*—Mark R. Gaworecki
(74) *Attorney, Agent, or Firm*—Lee & Hayes, PLLC

(57) ABSTRACT

Apparatus and methods of determining the chemical properties of a composite material using infrared spectroscopy are disclosed. In one embodiment, an apparatus for determining the chemical properties of a composite material includes an infrared source configured to project infrared energy towards an optical interface positioned on a surface of the composite material. An infrared detector then receives infrared energy gathered by the optical interface. One or more optical filters operable to transmit a respective range of wavelengths are positioned in the reflected beam.

21 Claims, 3 Drawing Sheets

APPARATUS AND METHODS OF DETERMINING CHEMICAL PROPERTIES OF A RESIN-BASED MATERIAL USING INFRARED ABSORBANCE

FIELD OF THE INVENTION

The present invention generally relates to composite materials, and more particularly, to an apparatus and methods of determining the chemical properties of a composite material using infrared spectroscopy.

BACKGROUND OF THE INVENTION

Composite materials are frequently used to form various structural components in applications where relatively low weight and high mechanical strength is desired. For example, composite materials are widely used in a variety of commercial and military aircraft, terrestrial vehicles and consumer products. A composite material is generally comprised of a network of reinforcing fibers and a polymeric resin that substantially wets the reinforcing fibers to form an intimate contact between the resin and the reinforcing fibers. The composite material may then be formed into a structural component by a variety of known forming methods, such as an extrusion process, a molding process, or other suitable forming processes.

In general, the composite fabrication process must be carefully monitored in order to obtain a composite material having the desired mechanical properties. For example, the composition of the resin and the reinforcing fiber must be carefully controlled so that the resin and the reinforcing fiber are combined so that the resin properly bonds to the fibers, and that no voids are formed within the composite material. The material may then be molded into a desired shape and cured, so that the material develops the desired mechanical properties and retains the desired shape. The degree of cure, in particular, may have a pronounced effect on material properties such as the strength and modulus. Typically, over-curing the material generates excessive cross-linking within the material, which may make the material excessively brittle. Correspondingly, under-curing the material may result in a molded component that exhibits insufficient rigidity.

One difficulty associated with the fabrication of composite materials is that various properties of the molded component must be determined by destructively testing the component. Alternately, a standard test sample may be fabricated and the test sample may be destructively tested to determine the mechanical properties of the composite material. The chemical properties of the composite material may be inferred from the outcome of the destructive test. In another known method, a sample of the composite material is removed and exposed to a solvent that dissolves the resin. Liquid chromatography is then used to determine the constituents present in the solvent. Since the sample is usually cut from the molded component, the remainder of the component must be discarded. Accordingly, inspection of composites using destructive testing methods may be expensive and wasteful.

Accordingly, what is needed in the art are apparatus and methods for determining the chemical properties of a resin material in a non-destructive manner.

SUMMARY OF THE INVENTION

The present invention comprises apparatus and methods of determining the chemical properties of a composite material using infrared spectroscopy. In one aspect, an apparatus for determining chemical properties of a composite material includes an infrared source configured to project infrared energy towards an optical interface positioned on a surface of the composite material. An infrared detector then receives infrared energy gathered by the optical interface. One or more optical filters each operable to transmit an appropriate wavelength band are positioned in the reflected beam.

BRIEF DESCRIPTION OF THE DRAWINGS

Embodiments of the present invention are described in detail below with reference to the following drawings.

DETAILED DESCRIPTION OF THE INVENTION

The present invention relates to apparatus and methods for determining chemical properties in a composite material using infrared absorbance. Many specific details of certain embodiments of the invention are set forth in the following description and in FIGS. 1 through 3 to provide a thorough understanding of such embodiments. One skilled in the art, however, will understand that the present invention may have additional embodiments, or that the present invention may be practiced without several of the details described in the following description.

Figure 1:
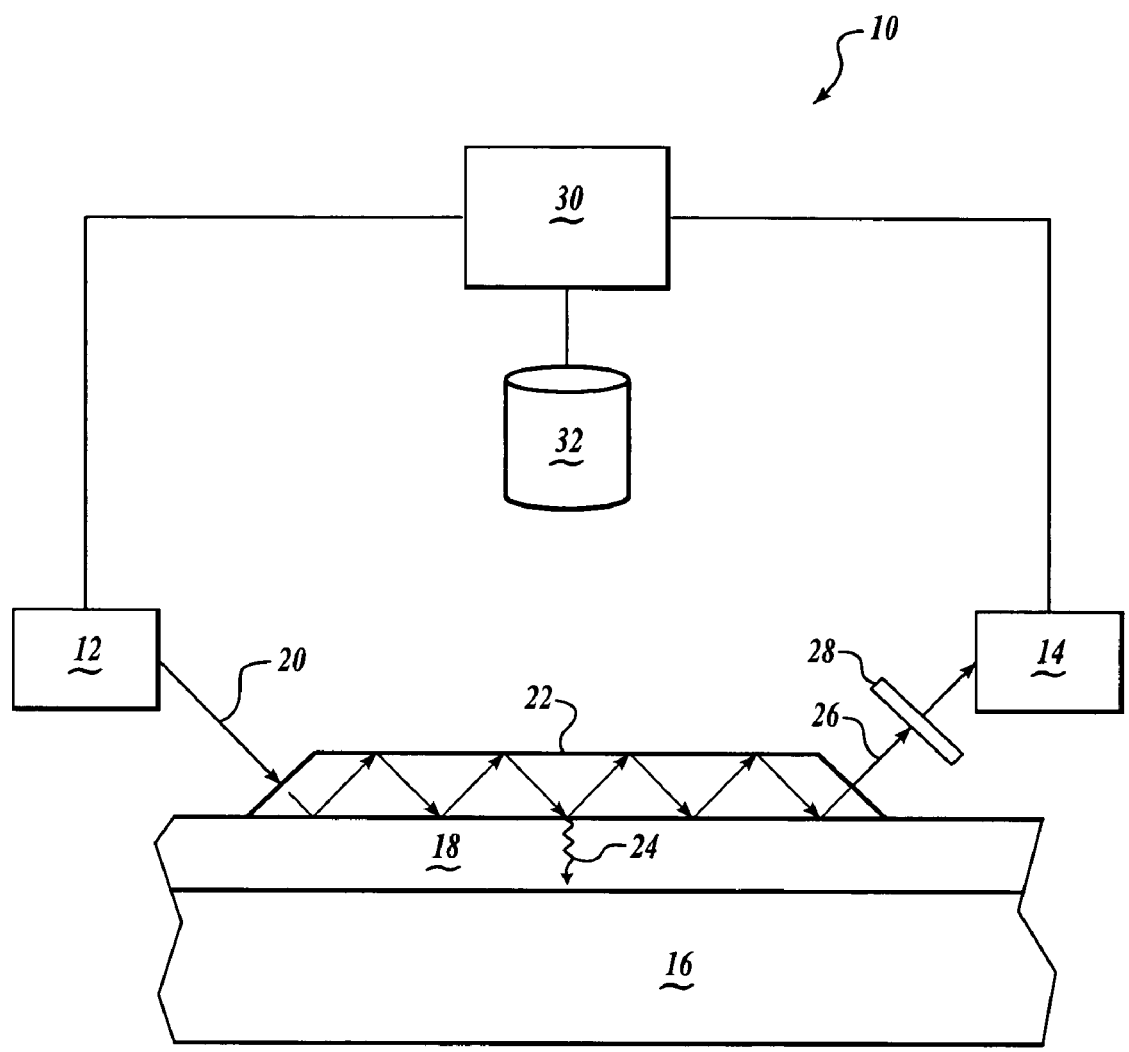
FIG. 1 is a diagrammatic view of an apparatus to determine the chemical properties of a composite material according to an embodiment of the invention.

FIG. 1 is a diagrammatic view of an apparatus 10 to determine the chemical properties of a composite material, according to an embodiment of the invention. Briefly and in general terms, the apparatus 10 permits selected chemical properties of a material to be determined nondestructively by measuring the infrared absorbance of the material at specified wavelengths. Accordingly, in one particular embodiment, the apparatus 10 includes an infrared source 12 and an infrared detector 14 that are spaced apart from a composite material 16. The infrared source 12 is configured to direct a transmitted beam 20 towards a surface layer 18 of the composite material 16, while the infrared detector 14 is configured to receive a reflected beam 26. An attenuation total reflection (ATR) crystal 22 may be positioned on the surface layer 18 so that at least one internal reflection occurs within the ATR crystal 22, and evanescent waves 24 are projected into the surface layer 18. Although a plurality of internal reflections are shown in FIG. 1, it is understood that as few as a single internal reflection may be present. The evanescent waves 24 are partially absorbed by the surface layer 18, which affect the spectral content of the reflected beam 26 that leaves the ATR crystal 22. In this embodiment, one or more optical filters 28 are positioned in a path of the reflected beam 26. The one or more filters 28 are operable to transmit a predetermined range of wavelengths in the reflected beam 26.

Figure 3:
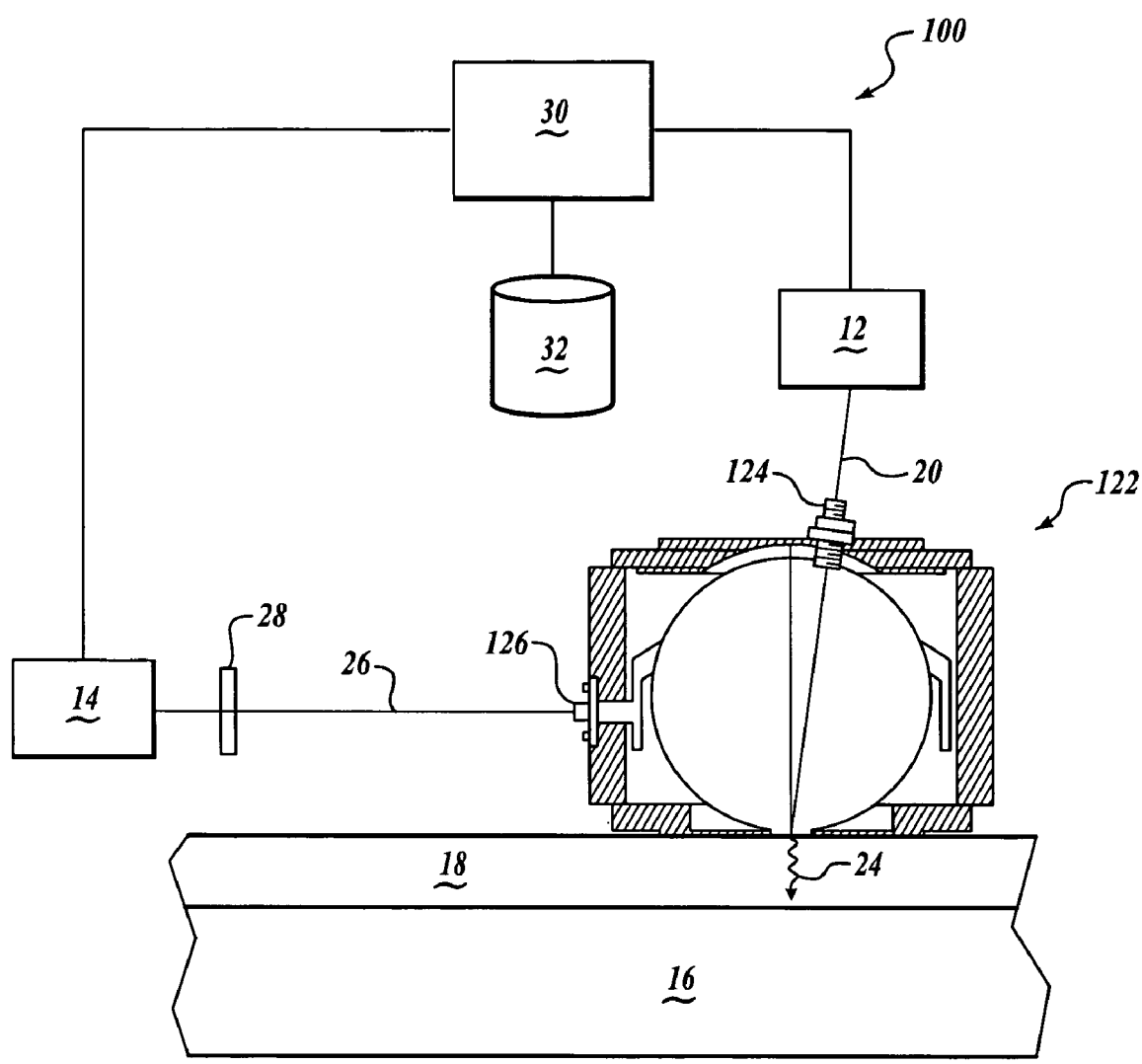
FIG. 3 is a diagrammatic view of an apparatus to determine the chemical properties of a composite material according to an alternate embodiment of the invention.

In another particular embodiment, the ATR crystal 22 may be omitted from the apparatus 10, and an integrating sphere (not shown in FIG. 1) may be positioned on the surface layer 18 of the composite material 16 so that a sampling aperture of the integrating sphere abuts the surface layer 18. For example, FIG. 3 is a diagrammatic view of an apparatus 100 that includes an integrating sphere 122 in accordance with an alternate embodiment of the invention. In this embodiment, the infrared source 12 is suitably positioned on the integrating sphere 122 to project the transmitted beam 20 through a first aperture 124 onto the surface layer 18. The relatively diffuse reflected beam 26 then exits the integrating sphere 122 through a measurement aperture 126 and is directed to the filter 28 and the infrared detector 14. The integrating sphere 122 may be any suitable device, including, for example, those integrating spheres commercially-available from Avantes, Inc. of Boulder, Colo.

In yet another particular embodiment, the ATR crystal 22 shown in FIG. 1 may be omitted so that the infrared source 12 projects the transmitted beam 20 directly onto the surface layer 18 and defines an illuminated region on the surface layer 18 having a predetermined size. A relatively specular reflected beam 26 is then directed from the surface 18 towards the filter 28 and the infrared detector 14. One example of a suitable infrared detector is an infrared spectrometer, such as the Surface Optics SOC 410 portable FT-IR spectrometer, which is available from the Surface Optics Corporation, of San Diego, Calif., although other suitable alternatives exist.

In still yet another particular embodiment, a barrel ellipse reflection device may be positioned on the surface layer 18 of the composite material 16 so that barrel ellipse reflection device abuts the surface layer 18.

As further shown in FIG. 1, the apparatus 10 also includes a processing system 30 that is operable to receive programmed instructions and data, and to process the data according to the received instructions. The processing system 30 may include various additional input/output devices (not shown) that permit a user to interact with the system 30, such as a display device, a keyboard, a pointing device or other suitable input/output devices. Additionally, the processing system 30 includes a data storage device 32 that is configured to store infrared intensity information received from the infrared source 12 and the infrared detector 14. Accordingly, the data storage device 32 may be a magnetic disk drive, or alternately, the data storage device 32 may include a semiconductor data storage device, such as a flash memory device or other suitable semiconductor memory devices.

Still referring to FIG. 1, the operation of the apparatus 10 will now be described in detail. The composite material 16 is brought into contact with the ATR crystal 22 and the transmitted beam 20 is projected towards the crystal 22 to make an energy measurement that characterizes the participation of the crystal 22. The transmitted beam 20 is generally in the infrared wavelength region of the electromagnetic spectrum. In a specific embodiment, the transmitted beam 20 is approximately in a range of wavelengths that extend between 0.7 microns ($\mu m$) and 1000 $\mu m$. The transmitted beam 20 is at least partially absorbed by the crystal 22, and the reflected beam 26 is then collected by the infrared detector 14. A selected composite material 16 may be identified by abutting the composite material 16 against the crystal 22 and projecting the beam 20 towards the material 16. The reflected beam 26 is filtered by the optical filters 28 that selectively transmit a portion of the reflected beam 26. In general, the optical transmission range of the optical filters depends upon the family of materials to be identified. In a particular embodiment of the invention, two optical filters are provided that are optically transmissive at wavelengths between approximately about 4 $\mu m$ and approximately about 9 $\mu m$. In one specific embodiment, however, the two optical filters are optically transmissive at approximately about 6.11 $\mu m$ and approximately about 7.10 $\mu m$, which have been observed to be particularly effective in the identification of BMS8-212, BMS8-276 and BMS8-256 composite resins. Appropriate ratios are formed between the reflected values obtained from the composite and the reflected value obtained from the crystal 22. Absorbances may be calculated based upon the foregoing ratios according to the relation: $A(\lambda) = -\log_{10}(E(\lambda)/E_{cr})$, where $E(\lambda)$ corresponds to a reflected energy value from a selected composite corresponding to a selected wavelength, and $E_{cr}$ corresponds to a reflected energy value obtained from the crystal 22. Accordingly, absorbances A1, A2 and A3 may be calculated and compared to identify the composite material. Although the foregoing describes the use of an ATR crystal interface, it is understood that other optical interfaces may be employed, such as the integrating sphere 122 described above with reference to FIG. 3.

Figure 2:
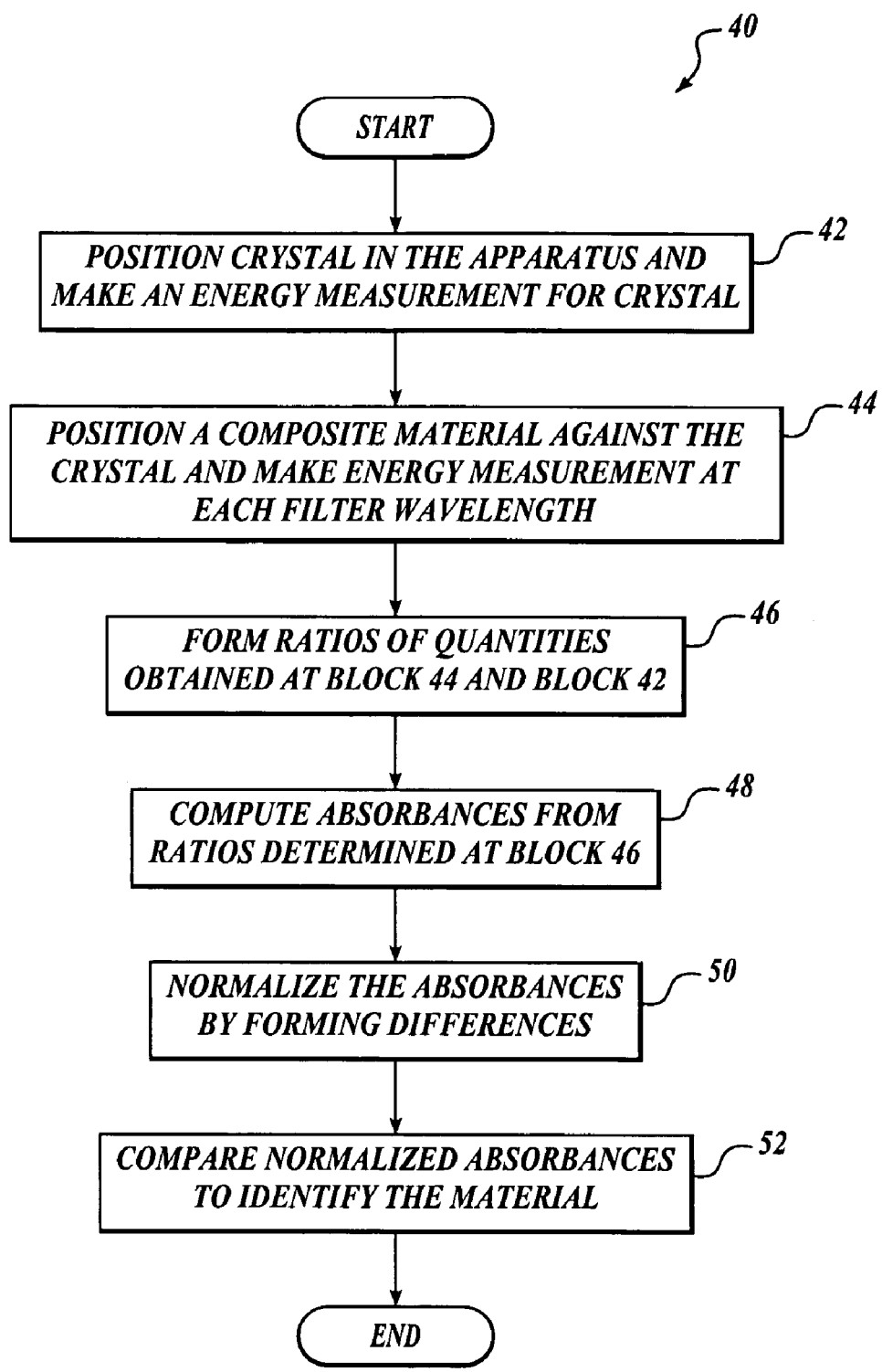
FIG. 2 is a method of determining a chemical property of a composite material in accordance with another embodiment of the invention.

FIG. 2 is a flowchart that will be used to describe a method 40 of determining a property of a resin-based composite material, according to an embodiment of the invention. At block 42, the crystal 22 is positioned in the apparatus of FIG. 1 and an energy measurement for the crystal 22 is made. At block 44, a composite material is positioned adjacent to the crystal 22 in the ATR crystal interface, or adjacent to the integrating sphere interface, or other similar interfaces, and the composite material is exposed to infrared radiation directed at the material by the source 12 (also shown in FIG. 1). At block 46, the reflected infrared energy values corresponding to the selected wavelengths are stored in the data storage device 32 (also shown in FIG. 1) and processed by the processing system 30 to form ratios between the reflected infrared energy values and the energy value associated with the crystal 22. The processor may also compute absorbance values based upon the foregoing ratios, as shown in block 48. The absorbances may also be normalized by subtracting a selected one of the absorbance values from the other computed absorbance values, as shown in block 50. At block 52, the normalized values are compared to identify a selected composite material. For example, if a first selected normalized absorbance is greater than zero, a first composite material is identified. If a second selected normalized absorbance is less than zero, a second composite material is identified. If a third selected normalized absorbance is approximately equal to zero, a third composite material is identified.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. An apparatus for determining chemical properties of a composite material, comprising:
   an infrared source configured to project infrared energy towards an optical interface positioned on a surface of the composite material, wherein the optical interface includes one of a barrel ellipse diffuse reflection device, an integrating sphere and an attenuation reflection crystal;

an infrared detector configured to receive infrared energy emitted by the optical interface; and one or more optical filters operable to transmit a respective range of wavelengths in the reflected beam, the one or more optical filters being interposed between one of the barrel ellipse diffuse reflection device, the integrating sphere, and the attenuation reflection crystal and the infrared detector.

2. The apparatus of claim 1, wherein-the-optical interface further comprises an attenuation reflection crystal (ATR) positioned on the surface of the composite material.

3. The apparatus of claim 2, wherein the infrared source is configured to emit infrared energy in a range of wavelengths between approximately about 0.7 microns ($\mu$m) and approximately about 1000 $\mu$m.

4. The apparatus of claim 1, further comprising a processing system operatively coupled to at least the infrared detector and configured to process information received from the infrared detector.

5. The apparatus of claim 4, wherein the processing system further comprises a data storage device.

6. An apparatus for determining chemical properties of a composite material, comprising:

an infrared source configured to project infrared energy towards an optical interface positioned on a surface of the composite material;

an infrared detector configured to receive infrared energy emitted by the optical interface; and one or more optical filters operable to transmit a respective range of wavelengths in the reflected beam, the one or more optical filters being interposed between the optical interface and the infrared detector, wherein the one or more optical filters further comprise optical filters configured to selectively transmit infrared energy at wavelengths between approximately about 4 microns ($\mu$m) and approximately about 9 $\mu$m.

7. The apparatus of claim 6, wherein the one or more optical filters further comprises a first optical filter having an admittance wavelength centered between approximately about 5 microns ($\mu$m) and approximately about 7 $\mu$m, and a second optical filter having an admittance wavelength centered between approximately about 7 microns ($\mu$m) and approximately about 9 $\mu$m.

8. The apparatus of claim 7, wherein the one or more optical filters further comprises a first optical filter having an admittance wavelength centered at about 6.11 microns ($\mu$m), and a second optical filter having an admittance wavelength centered at about 7.10 $\mu$m.

9. A method of determining a property of a resin-based composite material using an apparatus having an infrared source, an infrared detector, an optical interface and at least one optical filter interposed between the source and the detector, comprising:

projecting infrared energy towards the optical interface to obtain an interface energy measurement;

projecting infrared energy towards a composite material and selectively filtering infrared energy emitted by the material to obtain composite material energy measurements;

processing the interface energy measurement and the composite material energy measurements to form processed values; and identifying the composite material based upon the processed values.

10. The method of claim 9, wherein processing the interface energy measurement and the composite material energy measurements to form processed values comprises forming ratios between the composite material energy measurements and the interface energy measurement and computing absorbance values based upon the ratios.

11. The method of claim 10, wherein processing the interface energy measurement and the composite material energy measurements to form processed values comprises normalizing the respective absorbance values.

12. The method of claim 9, wherein selectively filtering the infrared energy comprises filtering the energy through optical filters configured to selectively transmit infrared energy at wavelengths between approximately about 4 microns ($\mu$m) and approximately about 9 $\mu$m.

13. A method of determining a property of a resin-based composite material using an apparatus having an infrared source, an infrared detector, an optical interface and at least one optical filter interposed between the source and the detector, comprising:

projecting infrared energy towards the optical interface to obtain an interface energy measurement, wherein projecting infrared energy towards a composite material comprises projecting infrared energy in a range of wavelengths between approximately about 0.7 microns ($\mu$m) and approximately about 1000 $\mu$m;

projecting infrared energy towards a composite material and selectively filtering infrared energy emitted by the material to obtain composite material energy measurements;

processing the interface energy measurement and the composite material energy measurements to form processed values;

identifying the composite material based upon the processed values; and selectively filtering the infrared energy comprises filtering the energy through optical filters configured to selectively transmit infrared energy at wavelengths between approximately about 4 microns ($\mu$m) and approximately about 9 $\mu$m.

14. The method of claim 13, wherein selectively filtering the infrared energy comprises filtering the energy through a first optical filter a first optical filter having an admittance wavelength centered at about 6.11 microns ($\mu$m), and a second optical filter having an admittance wavelength centered at about 7.10 $\mu$m.

15. A method of determining a property of a resin-based composite material using an apparatus having an infrared source, an infrared detector, an optical interface and at least one optical filter interposed between the source and the detector, comprising:

projecting infrared energy towards the optical interface to obtain an interface energy measurement, wherein projecting infrared energy towards a composite material comprises exposing the composite material to infrared energy in a range of wavelengths between approximately about 0.7 microns ($\mu$m) and approximately about 1000 $\mu$m;

projecting infrared energy towards a composite material and selectively filtering infrared energy emitted by the material to obtain composite material energy measurements;

processing the interface energy measurement and the composite material energy measurements to form processed values;

identifying the composite material based upon the processed values; and selectively filtering the infrared energy comprises filtering the energy through optical filters configured to selectively transmit infrared energy at wavelengths between approximately about 4 microns (μm) and approximately about 9 μm.

16. The method of claim 15, wherein selectively filtering the infrared energy comprises filtering the energy through a first optical filter a first optical filter having an admittance wavelength centered at about 6.11 microns (μm), and a second optical filter having an admittance wavelength centered at about 7.10 μm.

17. A method of identifying a resin-based composite material, comprising:
   projecting infrared energy towards a surface of a composite material;
   collecting infrared energy emitted by the surface and processing the collected energy to generate processed results; and
   comparing the processed results to identify the material, wherein comparing the processed results comprises computing normalized absorbance values and determining if the normalized absorbance value is less than zero, greater than zero, and approximately equal to zero.

18. The method of claim 17, wherein projecting infrared energy towards a surface of a composite material comprises projecting infrared energy in a range of wavelengths between approximately about 0.7 microns (μm) and approximately about 1000 μm.

19. The method of claim 17, wherein comparing the processed results further comprises correlating a normalized value with a selected composite material.

20. The method of claim 17, wherein collecting infrared energy emitted by the surface the further comprises filtering the infrared energy to encompass energy at wavelengths between approximately about 4 microns (μm) and approximately about 9 μm.

21. A method of identifying a resin-based composite material, comprising:
   projecting infrared energy towards a surface of a composite material;
   projecting infrared energy towards an optical interface and acquiring an interface energy value;
   collecting infrared energy emitted by the surface and processing the collected energy to generate processed results; and
   comparing the processed results to identify the material.

* * * * *